United States Patent
Kaya

(10) Patent No.: US 8,907,677 B2
(45) Date of Patent: Dec. 9, 2014

(54) ELECTROCHEMICAL SENSOR AND METHOD FOR THE PRODUCTION THEREOF

(75) Inventor: Alexander Kaya, Griesheim (DE)

(73) Assignee: Nanoscale Systems, Nanoss GmbH, Darmstadt (DE)

( * ) Notice: Subject to any disclaimer, the term of this patent is extended or adjusted under 35 U.S.C. 154(b) by 646 days.

(21) Appl. No.: 13/125,423

(22) PCT Filed: Oct. 22, 2009

(86) PCT No.: PCT/EP2009/007563
§ 371 (c)(1),
(2), (4) Date: Sep. 15, 2011

(87) PCT Pub. No.: WO2010/046105
PCT Pub. Date: Apr. 29, 2010

(65) Prior Publication Data
US 2012/0019258 A1   Jan. 26, 2012

(30) Foreign Application Priority Data
Oct. 22, 2008  (DE) .......................... 10 2008 052 645

(51) Int. Cl.
*G01N 27/62* (2006.01)
*G01N 27/12* (2006.01)
*B82Y 15/00* (2011.01)

(52) U.S. Cl.
CPC .............. *G01N 27/127* (2013.01); *B82Y 15/00* (2013.01)
USPC ....................................... 324/464; 204/228.7

(58) Field of Classification Search
USPC ..................... 204/228.6, 228.7; 324/459–470
See application file for complete search history.

(56) References Cited

U.S. PATENT DOCUMENTS

| | | | |
|---|---|---|---|
| 4,674,320 A | 6/1987 | Hirschfeld | |
| 4,900,405 A * | 2/1990 | Otagawa et al. | ............... 205/781 |
| 7,253,004 B2 | 8/2007 | Vossmeyer et al. | |
| 7,997,125 B2 | 8/2011 | Kaya et al. | |
| 2003/0012953 A1 | 1/2003 | Yadav et al. | |

(Continued)

FOREIGN PATENT DOCUMENTS

DE    699 22 776 T2    12/2005
DE   102006004922 A1    8/2007

(Continued)

OTHER PUBLICATIONS

I. Utke, et al., "Gas-assisted focused electron beam and ion beam processing and fabrication" Journal of Vacuum Science and Technology B, vol. 26, No. 4, Jul./Aug. 2008, p. 1197-1276.*

(Continued)

*Primary Examiner* — J. Christopher Ball
(74) *Attorney, Agent, or Firm* — Laurence A. Greenberg; Werner H. Stemer; Ralph E. Locher

(57) ABSTRACT

An electrochemical sensor allows even extremely small quantities or concentrations of a target chemical substance to be detected or quantified with a high precision in a particularly reliable manner. The novel sensor has a detector zone formed by nanoparticles which are embedded in a matrix and have a higher electric conductivity than the matrix material. The electric conductivity of the zone is determined by electron tunneling, ionization or hopping processes among the nanoparticles and by the electrochemical interaction thereof with a target substance to be detected.

20 Claims, 3 Drawing Sheets

(56) References Cited

U.S. PATENT DOCUMENTS

| | | |
|---|---|---|
| 2006/0003097 A1 | 1/2006 | Andres et al. |
| 2007/0114138 A1 | 5/2007 | Krasteva et al. |
| 2007/0258147 A1 | 11/2007 | Van Der Boom et al. |
| 2008/0245675 A1 | 10/2008 | Joseph et al. |
| 2010/0273665 A1 | 10/2010 | Haick et al. |

FOREIGN PATENT DOCUMENTS

| | | |
|---|---|---|
| EP | 0869353 A2 | 10/1998 |
| EP | 1278061 A1 | 1/2003 |
| EP | 1790977 A1 | 5/2007 |
| EP | 1975605 A1 | 10/2008 |
| WO | 2005015792 A2 | 2/2005 |
| WO | 2007088018 A1 | 8/2007 |
| WO | 2009066293 A1 | 5/2009 |

OTHER PUBLICATIONS

Thurier, C. & P. Doppelt, "Platinum OMCVD processes and precursor chemistry", Coordination Chemistry Reviews, vol. 252, Jan. 2008, p. 155-169.*

Brenig, W., et al., "Kinetic theory of hopping conductivity in amorphous solids", Physics Letters, A, vol. 35, No. 2, May 1971, p. 75-76, Abstract only.*

"Ceramic Laboratory Practice (327-0504-00)", Jan. 13 to Apr. 29, 2004, Department of Materials, ETH (Swiss Federal Institut of Technology), Zürich, Switzerland.

* cited by examiner

ELECTROCHEMICAL SENSOR AND METHOD FOR THE PRODUCTION THEREOF

BACKGROUND OF THE INVENTION

Field of the Invention

The invention relates to an electrochemical sensor, in particular for the detection and/or quantification of chemical substances or materials in extremely small quantities or concentrations. It furthermore relates to a method for producing a sensor of this type.

Highly sensitive sensors for detecting even extremely small quantities or concentrations of selected chemical substances can be used in a large number of applications. Sensors of this type can advantageously be used in particular in the measurement of extremely small quantities of chemical and biochemical substances, such as gases or biomolecules, e.g. in the following fields:
- environmental protection, in the measurement of air quality and water quality
- military and homeland protection, in the detection of toxic or explosive substances
- chromatography
- use as "artificial noses" in quality assurance, e.g. in the foodstuffs, beverages or perfume industry

BRIEF SUMMARY OF THE INVENTION

The invention is based on the object of specifying a sensor, in particular an electrochemical sensor, with which even extremely small quantities or concentrations of a chemical target substance can be detected or quantified with high accuracy in a particularly reliable manner. Furthermore, the intention is to specify a particularly suitable method for producing a sensor of this type.

With regard to the sensor, this object is achieved according to the invention with a detector zone, the electrical conductivity of which is determined by electronic tunneling, ionization or hopping processes, in particular between localized states or nanoparticles, and the electrochemical interaction thereof with a target substance to be detected.

In this case, the invention is based on the consideration that the sensor should expediently be oriented toward an electrical or electronic measurement principle with regard to the measurement values or signals yielded exhibiting utilizability and further processability that are as expedient as possible. In order in this case to provide the particularly high sensitivity desired with regard to the presence of particles of the chemical target substance, therefore, a sensor parameter that is particularly readily accessible from a metrological standpoint, that is to say, in particular, the conductivity or electrical resistance of said sensor, should be predetermined in such a way that the sensor reacts even to extremely small changes in the number of particles or concentration of the chemical target substance in its vicinity very sensitively with a comparatively greatly pronounced change in its electrical conductivity or its electrical resistance.

This can be achieved by providing a system in a detector zone wherein, by means of electrically insulated nanoparticles, dopings, defects or traps or by means of structural disorder, localized states or a zero-dimensional electron gas or energy states trapped in some other way are formed for charge carriers. Charge transport can then take place only in thermally activated fashion upon the supply of an assisting external electrical, electromagnetic or thermal activation energy. Possible conduction mechanisms are: the so-called hopping mechanism, field emission or, ionization effect, Poole-Frenkel effect or a differently configured tunnel effect of the electrons between the localized sites or defects or traps. This, is because precisely in the case of systems of this type, wherein the electron transport is based substantially on tunnel, ionization or hopping effects, the electrical conductivity is extremely dependent on the electrical coupling of the individual localized states to one another.

This in turn is dependent, given suitable configuration of the other system parameters such as, for example, material choice, geometry parameters, average distance between the localized states and the like, very sensitively on the electrochemical interaction with the target substance, such that even in the case of extremely small changes in the concentration or quantity of particles of the target substance in the vicinity of the detector zone, comparatively large effects on the electrical conductivity are obtainable, particularly since the electrical parameters such as resistance or conductivity in the case of systems of this type change exponentially with the coupling strength between the tunneling partners, which coupling strength can be influenced by said interaction.

In this case, the electrochemical interaction of said tunneling or hopping processes with the target substance to be detected can be effected directly, in particular by contact between the carrier medium loaded with the target substance and the detector zone or indirectly, that is to say across certain short distances. In particular, in this case, as a result of contact or interaction of the target substance present in the gaseous or liquid phase with the detector zone of the sensor, an exchange of electrons or ions or else an electrostatic or electromagnetic interaction between the sensor and the target substance can take place, which alters the electron concentration or the electron mobility in the material of the detector zone and/or, in particular, the coupling between the nanoparticles. Thus, even inherently electrically neutral substances such as water, for example, can be detectable since dipole moments can also disturb the local electron concentration in the detector zone.

In the case of the dominance of hopping processes for the electrical conductivity $\sigma(T)$ of the detector zone, which occurs in generally disordered, structureless systems such as amorphous silicon, for example, for said detector zone the temperature dependence of its electrical conductivity is preferably given approximately by the relation $\ln \sigma \sim T^{-\gamma}$. In this case, the detector zone is advantageously configured in such a way that the characteristic exponent $\gamma$ of this relationship has a value of between 0 and 1, preferably approximately the value 0.25, approximately the value 0.5 or approximately the value 1.

Advantageously, the detector zone is formed from nanoparticles embedded into a matrix, said nanoparticles having a higher electrical conductivity in comparison with the matrix material.

In order to ensure the intended dominance of the electronic tunneling, ionization or hopping processes for the electrical conductivity of the detector zone, the material forming the latter advantageously has a particularly suitable morphology. In particular, the morphology in the detector zone is in this case preferably chosen in such a way that a multiplicity of zones having a comparatively small extent and having a comparatively high electrical conductivity are formed, which adjoin one another or are connected to one another via intermediate zones having a comparatively low electrical conductivity. For this purpose, the material forming the detector zone could have an amorphous, nano- or polycrystalline structure, for example. Advantageously, however, the detector zone is formed from nanoparticles embedded into a matrix composed of suitably selected, in particular non-conductive, material having a comparatively low electrical conductivity, said nanoparticles having a higher electrical conductivity in comparison with the matrix material. Such locally changing zones having low and high conductivity are thus formed, for example, by composite systems composed of conductive nanocrystallites, defects or traps or dopings embedded in an electrically insulating matrix (base medium). Such systems characterized by a nanocrystalline construction are also designated as nanocomposites.

In this case, the nanoparticles can be formed from material having a suitably high electrical conductivity, for example from semiconducting or superconducting material. However, a setting of desired properties that is particularly compliant with requirements can be achieved by means of the nanoparticles advantageously being formed in metallic fashion, in particular from gold (Au), tungsten or platinum (Pl).

Preferably, inorganic, organic or dielectric material or else polymer material is provided for forming the matrix.

Advantageously, the material forming the detector zone, said material being provided as sensor-active material, is designed, with regard to the choice of its respective parameters, especially with a view to the desired great dependence of the electrical conductivity on the interaction with the target substance. In order to ensure this, in particular, the nanoparticles or the defects that bring about the localized states are selected, with regard to their size, distances, constitution and number density of particles upon embedding into the matrix, in a targeted manner and selectively with regard to the possible interaction with the target substance.

Moreover, said parameters are advantageously chosen suitably in such a way that the resulting electrical conductivity is substantially dominated by said electronic tunneling, ionization or hopping processes. In this case, the nanoparticles have, for example, an average particle size of up to 10 nm, preferably of up to 1 nm. Alternatively, however, particle sizes of up to 100 nm or more are also conceivable, provided that they are sufficiently electrically insulated from one another and their distances are sufficiently small, such that tunnel effects can be established between them. When setting the particle size, it is advantageously taken into account that, precisely when using the nanocomposites, the comparatively small particles, in comparison with larger particles, have a larger specific (internal) surface area, that is to say surface area in relation to the volume, such that they have a particularly high energetic reactivity with the target substance. Therefore, in principle, a sensor having a rough, nanocrystalline surface is more sensitive to an electrochemical reaction than a sensor having a smooth surface.

In one advantageous development, the detector zone is formed by a coating applied to a carrier body or a substrate.

Since the sensor is constructed on the basis of nanocomposites in its detector zone, it can be embodied in laterally very small dimensionings with recourse to particularly suitable production or deposition methods. As a result, the sensor, and in particular the detector zone thereof, in the manner of a nanosensor, can be positioned with pinpoint accuracy and in a manner compliant with requirements at an intended location—which, for example, is particularly suitable for the detection of the respective target substance—on a larger structure, for example a larger substrate. This also makes it possible, in particular, to equip a substrate with a comparatively complex system with different types of sensor functionalities. Thus, by way of example, in a simple manner, it is possible to provide a microarray or microgrid of nanosensors that are different in terms of equipment, size and/or design for interaction with target substances, each nanosensor advantageously being designed in each case for the detection of a specific type of chemical substance. Thus, in the manner of parallel detection or processing, mixed states of different chemicals or substances can also be detected in a single, simultaneous measurement step, which would otherwise have to be analyzed sequentially in a time-consuming manner. For the purposes mentioned, in a particularly advantageous configuration in a particularly advantageous configuration, a plurality of detector zones that differ from one another with regard to the material choice for the matrix and/or the nanoparticles and/or the size and/or density of the nanoparticles are arranged on a common carrier body.

In principle, various technologies are conceivable for producing the sensor and, in particular, the detector zone. However, one method which can be adapted particularly well to the design principles of the sensor, in particular to the provision of the detector zone, and is thus particularly suitable for production and with which the object in this regard is achieved according to the invention is deposition by local energy excitation, such as, for example, ion beam-induced, pyrolytically induced or photon beam-induced deposition, particularly advantageously electron beam-induced deposition (EBID). In this case, "local energy excitation" should be understood to mean, in particular, that the lateral extent of the depositions arising as a result of the energy excitation is significantly smaller, for example a few nm to a few µm, than the dimensions of the substrate, of a few 100 µm or a few mm, for example, that is used for the deposition. The methods mentioned are based on the physical and chemical transformation processes taking place under a scanned particle beam, consisting of electrons, ions or photons, or a beam of electromagnetic waves, in a precursor gas present at the beam location. This method enables, particularly with the aim of deposit structuring on a microscopic scale, a targeted material deposition of functional nanostructures, in which case, through the choice of suitable deposition parameters, a targeted spatial construction of the desired structures is possible in a manner limited to the spatial composition desired in the end product.

This means that a subsequent aftertreatment of structures once they have been deposited, in accordance with conventional methods such as, for example, by means of lithographic etching or the like, is not necessary to produce the desired spatial form in the miniaturized end product. In particular, specific silicon and mask techniques or semiconductor-based carrier substrates or a clean room environment are/is no longer, required. In this case, the deposit structuring process is based on the principle that molecules of a starting structural substance (precursor) which are in the gas phase and adsorb on a surface within a vacuum environment are excited by means of a locally concentrated incidence of energy, which can consist, for example, of focused electrons, ions or photons or other energetically concentrated objects, and are fixed by means of a decomposition or conversion process of their bonds as a sediment or deposit permanently on a surface of a substrate situated in the vicinity. In this case, the initial material deposit simultaneously serves as a seed for new deposits that are guided by the local position of the energy action and the residence duration thereof, such that any desired three-dimensional objects can be deposited on the substrate, depending on the focusability of the energy source with up to nanometer precision accuracy.

Through the suitable choice of the starting substances or precursor materials and also through the suitable choice of the parameters used during the deposition, process, in this case it is possible to influence the microscopic properties of the end product in a particularly flexible and far-reaching manner. In particular, it is possible to set both the size of the nanocrystallites and their distances and starting materials during the production process by means of the ambient parameters such as, for example, beam acceleration voltage, beam current, precursor material, etc., such that specific, targeted sensor materials coordinated with the interaction with a predeterminable target substance and having high selectivity relative to the respective target substance can be produced.

In order to ensure, in the detector zone, the desired great dependence of the electrical conductivity on the abovementioned interaction and the targeted and comparatively homogeneous distribution of nanoparticles in a suitable matrix, as provided for this purpose, in this case organic, inorganic, dielectric or organometallic complexes, monomers, oligomers, polymers or mixtures of said monomers, oligomers and polymers, which are preferably in the gas phase and have a vapor pressure that is particularly expedient for deposition, are advantageously used as precursor materials. Advantageously, in particular $CH_3$, $C_5O_2H_7$, $C_5O_2F_3H_4$, $C_5O_2F_6H$, $C_5H_5$, $Me_2Au(acac)$ [empirical formula: $(CH_3)_2AuC_5O_2H_7$], $Me_2Au(tfac)$ [empirical formula: $(CH_3)_2AuC_5O_2F_3H_4$], $Me_3Au(hfac)$ [empirical formula: $(CH_3)_2AuC_5O_2F_6H$], $Cu(hfac)_2$ [empirical formula: $Cu(C_5O_2F_6H)_2$], $CpPtMe_3$ (empirical formula: $C_5H_5Pt(CH_3)_3$], $CpMePtMe_3$ [empirical formula: $C_5H_4(CH_3)Pt(CH_3)_3$], $Mo(CO)_6$, $W(CO)_6$, $WF_6$, $[RhCl(PF_3)_2]_2$, $Co_2(Co)_8$, $AuCl(PF_3)$ and/or $Ni(CO)_4$, are/is used as precursor substance.

The abovementioned deposition method is suitable, in particular, both for producing a surface coating for producing the detector zone on a substrate serving as carrier body in the manner of subsequent refinement of the carrier body, and for producing a bulk body, wherein the base body of the sensor per se is already formed from the nanoparticles embedded into the matrix and thus forms in turn in its totality the detector zone. In order to produce such structures, advantageously an energetic particle beam provided for the energetic excitation of the precursor substances or a local pyrolytic treatment, for example by means of a laser beam, is guided, with respect to the substrate, laterally or three-dimensionally depending on a predetermined desired geometry of the deposit. In this case, in particular, a plurality of respectively mutually different detector zones for forming a complex sensor system can be deposited on a common substrate or carrier body.

Advantageously, the temperature of the substrate is regulated suitably during the deposition. This influences the speed of the surface diffusion processes on the substrate, which leads to a regulable subsequent supply rate of precursor material and thus to a controlled growth rate of the deposit. Alternatively, the subsequent supply rate can also be regulated by the temperature of the precursor source being increased or decreased, since this directly influences the vapor pressure of the precursor.

Alternatively, the pyrolytic or pyrolytically induced deposition can advantageously be used as well. In this case, solid deposits can also be deposited on a substrate by means of the substrate being heated after nondirectional adsorption of precursor molecules, for example from below by means of a heating wire or from above by means of a laser beam. The supply of energy then locally effects the desired conversion of the precursor materials.

By means of the application of the abovementioned deposit structuring, in particular by means of the production of the detector zone or else of the entire base body of the sensor by means of electron beam-induced deposition or else by means of ion beam-induced, pyrolytically induced or photon beam-induced deposition, it is possible to achieve a particularly high flexibility in the setting of desired properties of the end product. In particular, through the choice of a suitable structure for the matrix, not only is it possible to suitably set the electrical conductivity with the aim of the desired sensitivity in the event of a change in the interaction with the environment, rather a targeted influencing of the production parameters during the deposition of the structures also enables a targeted influencing of other microscopic properties.

The advantages achieved by means of the invention consist, in particular, in the fact that by virtue of the provision of a detector zone on the basis of nanoparticles embedded into a matrix, it is possible to achieve a particularly sensitive dependence of the electrical conductivity of the detector zone on changes in the ambient conditions of the sensor, in particular the particle density of the selected target substance, on an extremely small scale. Particularly sensitive measurements associated with extremely small changes in the quantity of the target substance can thus be carried out. The local concentration of the target substance can thus be measured particularly precisely, such that it is possible to provide highly accurate sensors on the basis of such measurements. The dependence of the electrical conductivity primarily on the coupling of the nanoparticles among one another also ensures, in particular, that the interaction with the particles of the target substance that are situated in the environment, by means of direct contact or else indirectly by means of electrical or magnetic interaction, results directly in a particularly sensitive dependence of the conductivity on the quantity or concentration of particles in the environment of the sensor. A particularly sensitive detection of particles of the target substance and also the quantitative determination thereof are thus possible, in which case even inherently electrically neutral substances such as water, for example, can also be detectable on account of their dipole moment.

Sensors of this type can advantageously be used for example in the measurement of extremely small quantities of chemical and biochemical substances, such as gases or biomolecules, e.g. in the following fields:
environmental protection, in the measurement of air quality and water quality
military and homeland protection, in the detection of toxic or explosive substances
chromatography
use as "artificial noses" in quality assurance, e.g. in the foodstuffs, beverages or perfume industry By means of the production of the detector zone or else of the entire sensor by means of deposit structuring methods such as, in particular, electron beam-induced deposition, the targeted production of microscopic structures with a high bandwidth of desired properties is additionally possible, in which case, in particular by means of suitable material and parameter selections, the electrical properties can be set particularly expediently and in a targeted manner and selectively with respect to the target substance chosen. In particular, the use of electron beam-induced deposition makes it possible to produce extremely miniaturized sensors or sensor elements, in which case, in particular, the detection geometry is virtually freely selectable.

An exemplary embodiment of the invention is explained in greater detail with reference to a drawing, in which:

DESCRIPTION OF THE INVENTION

Identical parts are provided with the same reference symbols in all the figures.

Figure 1:
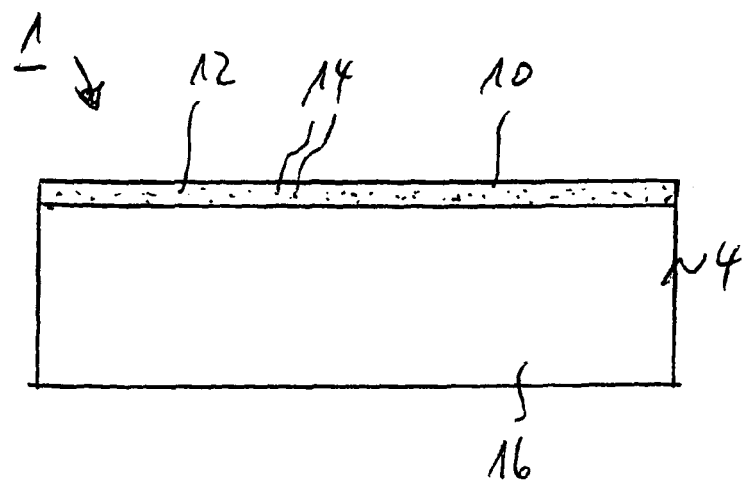
FIG. 1 shows a miniaturized electrochemical sensor.

The miniaturized sensor 1 in accordance with FIG. 1 is provided, in particular, for use as an electrochemical sensor for the detection and/or quantification of chemical materials or substances even in extremely small quantities or concentrations. Alternatively, however, a large number of further application possibilities in microsensor technology or biosensor technology or the like are also conceivable. The miniaturized sensor 1 comprises a substrate or a base body 4, which is provided with a detector zone 10, which is in turn formed by preferably metallic nanoparticles 14 embedded in a matrix 12. In this case, in the exemplary embodiment, the matrix 12 is configured as a polymer matrix into which the metallic nanoparticles 14 are embedded. In this case, the nanoparticles 14 form embedded localized states for electrical charges. Alternatively or additionally, these can also be formed by defects or traps or by structural disorder, for example in an amorphous medium.

However, the nanocrystals are not absolutely necessary for the sensor effect per se. They are advantageous in the operation of the sensor, however, since they additionally intensifies the sensor effect. This is achieved by virtue of the fact that the crystallites can be constructed with the aid of the proposed production method in such a way that they have diameters of the order of magnitude of 1 nanometer or less. These particles have a particularly increased ratio of surface area to volume. Therefore, on account of their microscopic roughness relative to the target substance to be detected they have a higher energetic reactivity or an increased effective sensor surface area relative to homogeneous bulk bodies having a smooth surface. External influences on the electrical conduction mechanisms, such as on the hopping or tunneling conductivity, are thereby promoted or intensified, and the electrochemical sensor effect is likewise intensified overall.

With regard to the material choice of matrix 12 and nanoparticles 14 and also with regard to the average particle size of approximately 1 nm in the exemplary embodiment and the density of the nanoparticles 14, the corresponding parameters are chosen in such a way that the electrical transport between the nanoparticles 14 within the matrix 12 is characterized by hopping processes and is guided by means of tunneling processes. Therefore, the conduction mechanism in the detector zone 10 is effected by means of the thermally activated hopping mechanism (hopping, nearest neighbor hopping, variable range hopping) between localized sites and arises as a result of a quantum mechanical tunnel effect. Complying with these boundary conditions ensures that the electrical conductivity of the detector zone 10 is very greatly and sensitively also dependent on the coupling between the nanoparticles 14 and thus on the electromagnetic environment of the sensor 1, such that this is detectable with high sensitivity and resolution.

In this case, the sensor 1 in accordance with FIG. 1 is constructed with recourse to a substrate of conventional design based on silicon, said substrate serving as a carrier body 16 and being provided with a superficial coating in order to form the detector zone 10. The design of the sensor 1 according to FIG. 1 thus corresponds to a refinement of a conventional substrate, wherein the detector zone 10 provided for the high measurement resolution desired is applied by a subsequent coating.

Since the deposition methods proposed for sensor production, such as electron beam-induced deposition, do not necessarily rely on silicon as a substrate support, the sensor, besides on silicon, can practically also be deposited on any other solid support desired. Consequently, the deposition method proposed is suitable, in a particularly flexible manner, for subsequently equipping or refining different materials, surfaces or already prefabricated or existing Structures with sensor functionality.

As an example, a "lab-on-a-chip" application shall be mentioned here which can have a large number of flow channels or measurement chambers for gases and liquids. Such lab-on-a-chip arrangements are usually prefabricated using silicon mask technology. The proposed method for the production of an electrochemical sensor would allow such a chip subsequently to be equipped with sensor functionality at any desired location.

The detector zone 10 of the sensor 1 and possibly also the entire base body 4 are produced by so-called deposit structuring, wherein particular growth of the respective structures is produced in and also restricted to those spatial regions in which the arising of the desired structures is provided. The subsequent, for example lithographic, etching required in the case of other miniaturized structures is thus obviated. In the exemplary embodiment, the method of so-called electron beam-induced or ion beam-induced deposition is provided for producing, the respective structures. In this case, a phase in which the corresponding structures arise is illustrated in FIG. 2.

Figure 2:
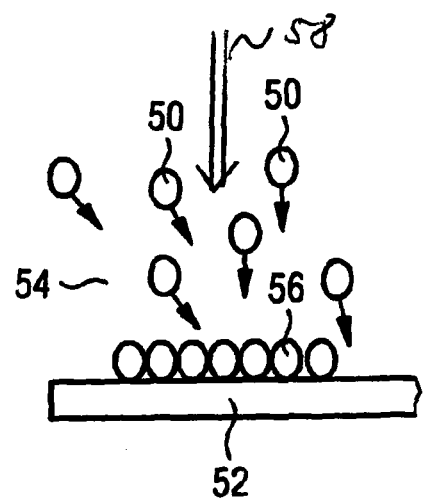
FIG. 2 shows a deposit growing on a substrate.

As can be gathered from the schematic illustration in FIG. 2, in a suitable environment, in particular in a vacuum, precursor substances, as illustrated in FIG. 2 on the basis of particles 50, are introduced in gaseous form into the vicinity of a substrate 52. As a result of adhesion forces between the precursor molecules and substrate, an adsorption of precursor material takes place on the substrate.

In a deposition zone 54 in direct proximity to the substrate 52, the precursor substances are energetically excited to conversion, in which case the conversion products deposit in solid and nonvolatile form as a sediment or deposit 56 permanently on the substrate 52. In this case, the initial material deposit on the substrate 52 simultaneously serves as a seed for new deposits that are guided by the local position of the energy effect and the residence duration thereof, such that virtually any desired three-dimensional objects can be produced on the substrate 52. In this case, the excitation for conversion and thus for deposition is effected by local energy excitation or application, an electron beam 58 being provided for this purpose in the exemplary embodiment. In terms of its lateral extent, said electron beam is significantly smaller than the surface of the substrate 52, such that the energy excitation actually takes place only locally and in a manner delimited to a comparatively small proportion of the substrate surface.

Figure 3:
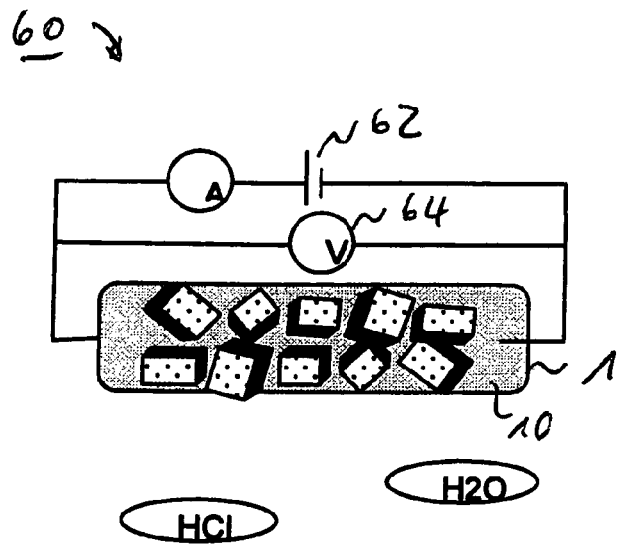
FIG. 3 shows a measuring arrangement comprising a sensor according to FIG. 1.

A measuring arrangement 60 comprising the sensor 1 is shown schematically in FIG. 3. In this case, the detector zone 10 of the sensor 1 is electrically connected to a current source 62, which can be embodied as a constant-current source, in particular. By means of a voltage sensor 64, the voltage V present across the detector zone 10 in the case of a predetermined current flow can be tapped off, such that the electrical resistance or the electrical conductivity of the detector zone 10 can be measured by means of this arrangement. This changes on account of the specific configuration of the detector zone 10 owing to its electrochemical interaction with a target substance to be detected in its environment, for example water ($H_2O$), hydrochloric acid (HCl) or the like.

Figure 4:
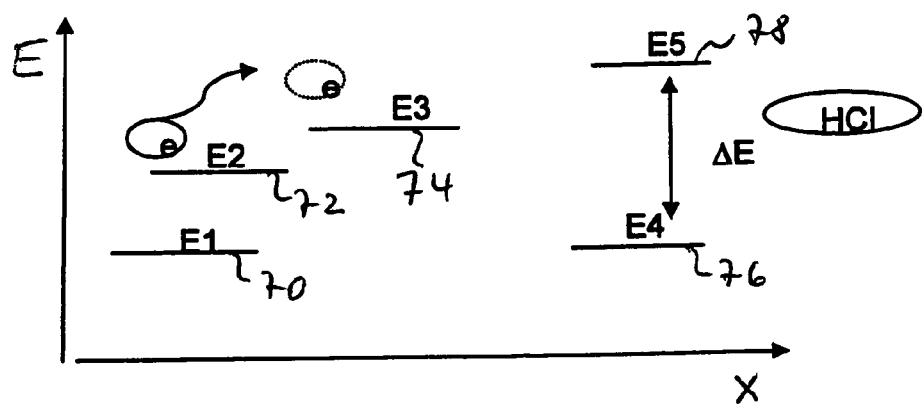
FIG. 4 shows a diagram with a number of energy levels.

In this case, the type of reaction of the detector zone 10 to the presence of the target substance is illustrated schematically in the energy diagram in accordance with FIG. 4. In this energy diagram, a location characteristic value is plotted on the x-axis and an energy value E is plotted on the y-axis. Localized electronic states characterized by their corresponding energy levels 70, 72, 74, 76, 78, as plotted in FIG. 4, are situated in the detector zone 10. In the example according to FIG. 4, the energy levels 70, 72, 74 in this case represent localized energy states between which an electron changes, places by means of a thermally activated hopping mechanism. In this case, the example according to FIG. 4 illustrates by way of example such a hopping process between the energy levels 72 and 74, which, for example, can also be assigned to two adjacent nanocrystallites 14.

Given the presence of a target substance to be detected, for example the chemical HCl, in the environment of the detector zone 10, the energetic distance between two adjacent localized energy states 76, 78 can be increased by the magnitude $\Delta E$ by means of electrical or electrochemical interaction with the target substance. Here the electron e would then have to surmount a greater energy magnitude, compared with the unchanged energy levels (such as, for example, the energy levels 72, 74), in order to change places assigned to the energy levels 76, 78. Thus, the electron mobility is reduced by the increase in energetic distance between said energy levels or the electrical resistance of the detector zone 10 is increased. Through the material choice in the detector zones 10 and also the concentration of the localized energy states, it is possible to effect an individualized adaptation of the detector zone 10 to an intended target substance and the interaction with the latter. This enables an individualized orientation of the reaction of the detector zone 10 to the presence of a desired target substance in the immediate environment.

Figure 5:
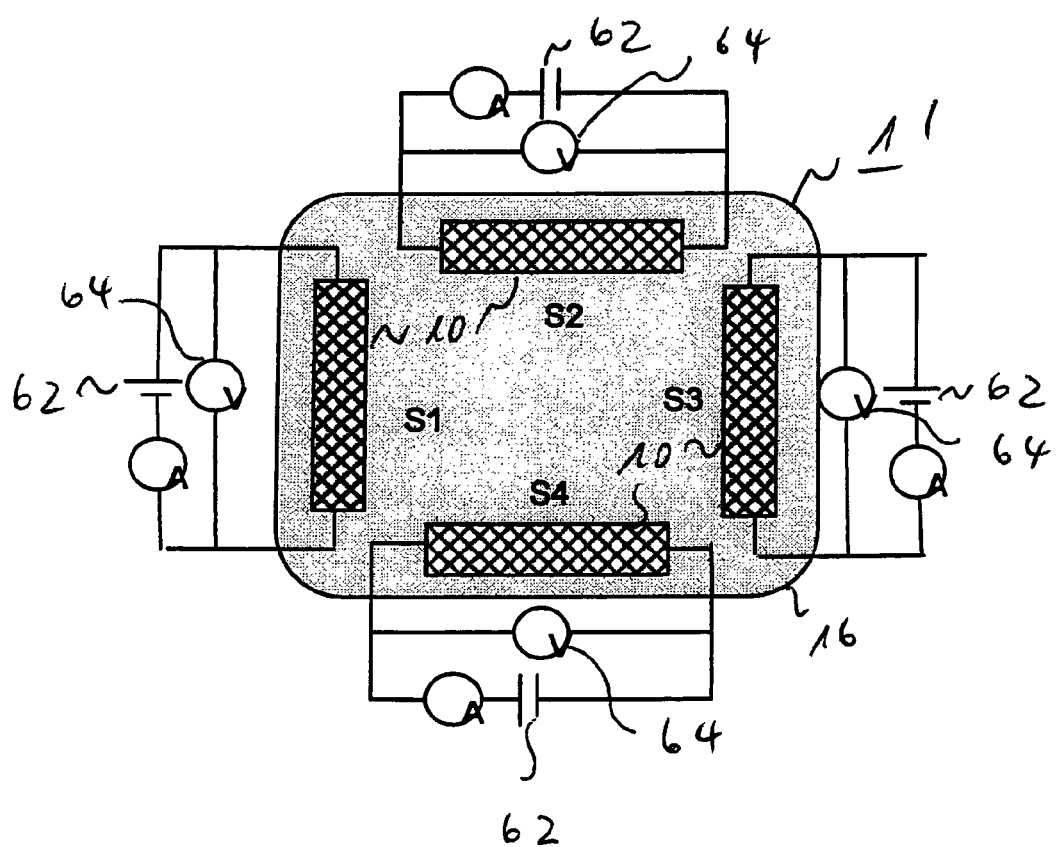
FIG. 5 shows the sensor according to FIG. 1 with a plurality of detector zones.

The exemplary embodiment according to FIG. 5 illustrates a sensor 1', wherein a plurality of detector zones 10 are arranged on a common carrier body 16. Said detector zones are in each case connected independently of one another to suitable current sources 62 and voltage sensors 64, such that their respective electrical resistance or their respective electrical conductivity can be measured independently of the others. Thus, a spatially resolved detection of the intended target substance is possible by virtue of a suitable spatial arrangement of the detector zones 10 relative to one another. Additionally or alternatively, the detector zones 10 can differ from one another with regard to the material choice of the matrix and/or the nanoparticles or their other microscopic properties and can thus be adapted to different target substances with regard to their interaction with the environment. Thus, with comparatively simple means, it is possible to provide a comparatively complex system with different sensor functionalities in the manner of a microarray or microgrid. Thus, in the manner of parallel detection or processing, mixed states of different chemicals or the like can also be detected in a single, simultaneous measurement step.

LIST OF REFERENCE SYMBOLS

1 Sensor
4 Base body
10 Detector zone
12 Matrix
14 Nanoparticles
16 Carrier body
50 Particles
52 Substrate
54 Deposition zone
56 Deposit
$\gamma$ Exponent
$\sigma$ Conductivity

The invention claimed is:

1. A method of producing an electrochemical sensor with a detector zone, the method which comprises:
providing a substrate and feeding a number of precursor substances in gaseous form to a deposition zone in a vicinity of a substrate;
energetically exciting the precursor substances for converting the precursor substances to form conversion products and causing the energetically excited conversion products to deposit in solid and nonvolatile form on the substrate, to thereby form the detector zone with an electrical conductivity determined by electron tunneling, ionization, or hopping processes and configured for detecting an electrochemical interaction thereof with a target substance to be detected by the electrochemical sensor; and
setting a plurality of process parameters so that the detector zone has a predetermined electrical conductivity dependent on a temperature T that is approximately governed by the relationship $\ln \sigma \sim T^{-\gamma}$, where $\sigma$ is the electrical conductivity and $\gamma$ is a characteristic exponent having a value of approximately 0.5 or approximately 1.0.

2. The method according to claim 1, wherein the step of producing the detector zone comprises applying energy by electron beam-induced deposition.

3. The method according to claim 1, which comprises selecting the precursor substances from the group consisting of organic, inorganic, dielectric or organometallic monomers, oligomers, and polymers.

4. The method according to claim 1, which comprises energetically exciting the precursor substances by ion beam, photon beam or electron beam irradiation and guiding the radiation, with respect to the substrate, laterally or three-dimensionally depending on a predetermined desired geometry of the deposition.

5. The method according to claim 1, which comprises controlling a temperature of the substrate and/or a temperature of a precursor source during the deposition in dependence on a vapor pressure of the precursor substances determined in the deposition zone.

6. The method according to claim 1, wherein the plurality of process parameters including to be set are selected from the group consistent of a type, a quantity, and a composition of the precursor substances, a gas pressure in the deposition zone, an intensity of the local application of energy, a duration of incidence thereof, a focus size thereof, a substrate material, and a substrate temperature.

7. An electrochemical sensor, comprising:
a substrate having a detector zone formed thereon with an electrical conductivity determined by electron tunneling, ionization, or hopping processes and configured for detecting an electrochemical interaction thereof with a target substance to be detected by the electrochemical sensor;
said detector zone being formed with nanoparticles deposited thereon by directed irradiation of precursor substances and energetic excitation thereof causing the nanoparticles to be deposited in the detector zone; and
wherein a dependence of the electrical conductivity of said detector zone on a temperature T is approximately governed by the relationship $\ln \sigma \sim T^{-\gamma}$, where $\sigma$ is the electrical conductivity and γ is a characteristic exponent having a value of approximately 0.5.

8. The electrochemical sensor according to claim 7, wherein said detector zone is formed from said nanoparticles embedded into a matrix, and said nanoparticles have a higher electrical conductivity than a material of the matrix.

9. The electrochemical sensor according to claim 7, wherein said nanoparticles are metallic nanoparticles.

10. The electrochemical sensor according to claim 9, wherein said metallic nanoparticles are formed of chemically stable materials.

11. The electrochemical sensor according to claim 9, wherein said metallic nanoparticles are formed from Au or Pt.

12. The electrochemical sensor according to claim 7, wherein said detector zone is a coating applied to a carrier body.

13. The electrochemical sensor according to claim 12, wherein said detector zone is one of a plurality of detector zones disposed on a common carrier body, said detector zones differing from one another with regard to a material of a matrix, a material of nanoparticles embedded in the matrix, and/or a size and/or density of the nanoparticles.

14. An electrochemical sensor, comprising:
a substrate having a detector zone formed thereon with an electrical conductivity determined by electron tunneling, ionization, or hopping processes and configured for detecting an electrochemical interaction thereof with a target substance to be detected by the electrochemical sensor;
said detector zone being formed with nanoparticles deposited thereon by directed irradiation of precursor substances and energetic excitation thereof causing the nanoparticles to be deposited in the detector zone; and
wherein a dependence of the electrical conductivity of said detector zone on a temperature T is approximately governed by the relationship $\ln \sigma \sim T^{-\gamma}$, where σ is the electrical conductivity and γ is a characteristic exponent having a value of approximately 1.

15. The electrochemical sensor according to claim 8, wherein said matrix is formed from one or more of the following materials: polymer material, organic or inorganic structural elements, carbon-based compounds, carbon-oxygen compounds, hydrogen compounds, fluorine compounds, and/or metal-containing structural elements.

16. The electrochemical sensor according to claim 8, wherein said matrix is formed from a material selected from the group consisting of organic material, inorganic material, or dielectric material.

17. The electrochemical sensor according to claim 8, wherein at least one of the materials forming said matrix or forming said nanoparticles is selected with a view to an expected interaction with the target substance to be detected.

18. The electrochemical sensor according to claim 8, wherein said nanoparticles have an average particle size of up to 100 nm.

19. The electrochemical sensor according to claim 8, wherein said nanoparticles have an average particle size of up to 10 nm.

20. The electrochemical sensor according to claim 8, wherein said nanoparticles have an average particle size of up to 1 nm.

* * * * *